(12) United States Patent
Bruder et al.

(10) Patent No.: US 8,750,588 B2
(45) Date of Patent: Jun. 10, 2014

(54) METHOD, COMPUTER READABLE MEDIUM AND SYSTEM FOR ITERATIVE IMAGE FILTERING WITH ANISOTROPIC NOISE MODEL FOR A CT IMAGE

(75) Inventors: Herbert Bruder, Höchstadt (DE);
Rainer Raupach, Heroldsbach (DE);
Johan Sunnegardh, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 253 days.

(21) Appl. No.: 13/207,507

(22) Filed: Aug. 11, 2011

(65) Prior Publication Data

US 2012/0039518 A1 Feb. 16, 2012

(30) Foreign Application Priority Data

Aug. 12, 2010 (DE) .......................... 10 2010 034 099

(51) Int. Cl.
*G06K 9/00* (2006.01)
(52) U.S. Cl.
USPC ......................................................... 382/131
(58) Field of Classification Search
USPC .................. 382/128–134; 128/920–925;
356/39–49; 600/407–414, 424–426;
345/581–618
See application file for complete search history.

(56) References Cited

U.S. PATENT DOCUMENTS

| 2003/0161548 A1* | 8/2003 | Vuylsteke ..................... 382/274 |
| 2007/0196008 A1* | 8/2007 | Borsdorf et al. ............... 382/131 |
| 2011/0052030 A1 | 3/2011 | Bruder et al. |

FOREIGN PATENT DOCUMENTS

DE 102009039987 A1 3/2011

OTHER PUBLICATIONS

J. Sunnegardh et al.: "Regularized iterative weighted filtered backprojection for helical cone-beam CT", Med. Phys. vol. 35, Sep. 2008, p. 4173-4185; Others; 2008.
German priority document DE 10 2010 034 099.5 filed Aug. 12, 2010, not yet published.

* cited by examiner

*Primary Examiner* — Atiba O Fitzpatrick
(74) *Attorney, Agent, or Firm* — Harness, Dickey & Pierce, P.L.C.

(57) ABSTRACT

The method includes a weighted highpass filtering of the image data takes place here, with the weighting taking account, image element by image element, of an image noise on the respective image element in different directions such that increasing noise results in a stronger highpass effect. A noise-reducing smoothing of the image data takes place using the weighted highpass filtering.

22 Claims, 4 Drawing Sheets

METHOD, COMPUTER READABLE MEDIUM AND SYSTEM FOR ITERATIVE IMAGE FILTERING WITH ANISOTROPIC NOISE MODEL FOR A CT IMAGE

PRIORITY STATEMENT

The present application hereby claims priority under 35 U.S.C. §119 on German patent application number DE 10 2010 034 099.5 filed Aug. 12, 2010, the entire contents of which are hereby incorporated herein by reference.

FIELD

At least one embodiment of the invention relates to the processing of computed tomography image data for noise reduction.

BACKGROUND

Generally, in tomographic imaging methods inner structures of an examination object can be examined without operations having to be performed on the object. One possible type of tomographic image generation consists in recording a number of projections of the object to be examined from different angles. A two-dimensional sectional image or a three-dimensional volume image of the examination object can be calculated from these projections.

One example of a tomographic imaging method is computed tomography. Methods for scanning an examination object using a CT system are generally known. For example, circular scannings, sequential circular scannings with feed or spiral scannings are used. Other types of scannings, which are not based on circular movements, are also possible (e.g., scans with linear segments). Absorption data of the examination object is recorded from different recording angles with the aid of at least one x-ray source and at least one opposite detector and this thus collected absorption data and/or these projections are allocated to sectional images through the examination object by way of corresponding reconstruction methods.

A so-called Filtered Back Projection (FBP) is typically used as the standard method for reconstructing computed tomography images from x-ray CT data records of a computed tomography device (CT device), i.e. from the captured projections. A so-called "rebinning" step is usually carried out after the data acquisition, in which step the data generated with the beam which propagates from the source in a fan-type fashion is rearranged such that it exists in a form as if the detector was hit by x-ray beams heading in parallel for the detector. The data is then transformed into the frequency range. A filtering takes place in the frequency range, and the filtered data is then transformed back. A back projection onto the individual voxels within the volume of interest then takes place with the aid of the thus rearranged and filtered data.

During the acquisition of the CT measurement data, the examination object, generally a patient, is exposed to a dose of x-ray radiation. Because this radiation is generally not harmless to the examination object, attempts are made to manage with as low a radiation exposure as possible. The dose used is nevertheless directly connected to the image noise in the image data reconstructed from the CT measurement data. A reduction in the dose results in an increase in the noise. In order to utilize as effectively as possible a specific radiation dose, it is therefore desirable to use image reconstruction or image processing methods which efficiently reduce the noise in CT images.

SUMMARY

Example embodiments include a control and computing unit, a CT system, a computer program and a computer program product methods for processing computed tomography image data, which effects a noise reduction.

At least one embodiment of the invention is directed to a method for processing computed tomography image data, new image data is obtained by a noise-reducing processing of the image data, whereby a weighted highpass filtering of the image data takes place, with the weighting taking account, image element by image element, of an image noise on the respective image element in different directions such that increasing noise results in a stronger highpass effect. A noise-reducing smoothing of the image data takes place using the weighted highpass filtering.

BRIEF DESCRIPTION OF THE DRAWINGS

The invention is explained in more detail below with the aid of example embodiments, in which.

Figure 1:
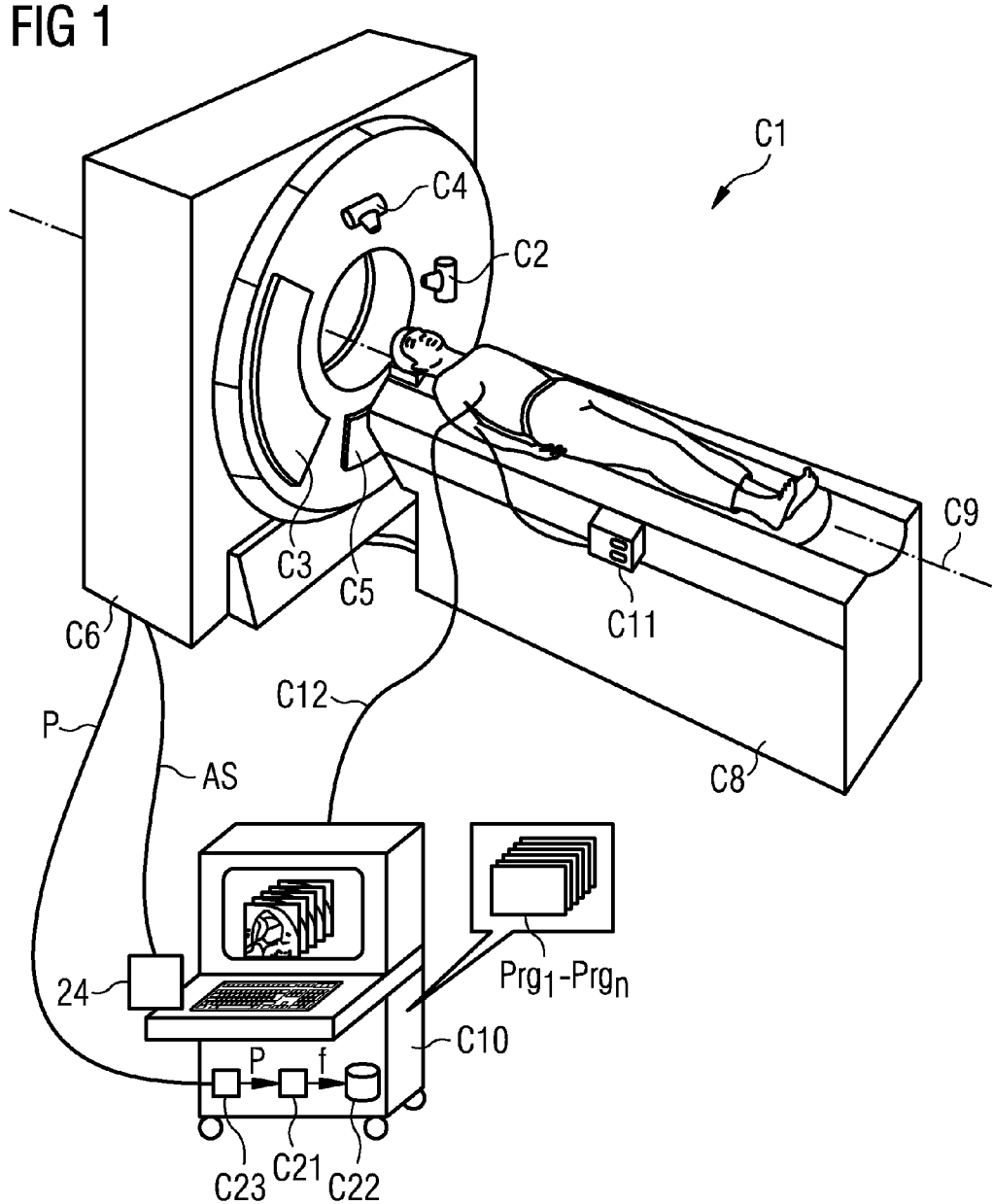
FIG. 1: shows a schematic representation of an exemplary embodiment of a computed tomography system with an image reconstruction component.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved. Spatially relative terms, such as "beneath", "below", "lower", "above", "upper", and the like, may be used herein for ease of description to describe one element or feature's relationship to another element(s) or feature(s) as illustrated in the figures.

It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic representation of a computed tomography system C1 with an image reconstruction facility C21. A closed gantry (not shown here) is found in the gantry housing C6, a first x-ray tube C2 being arranged with an opposite detector C3 on said closed gantry. A second x-ray tube C4 with an opposite detector C5 is optionally arranged in the CT system shown here, so that a higher time resolution can be achieved by way of the emitter/detector combination which is also available, or "dual energy" examinations can also be carried out with the use of different x-ray energy spectra in the emitter/detector systems.

The CT system C1 also has a patient couch C8, on which a patient can be moved during the examination along a system axis C9, also referred to as the z-axis, into the measurement field, with it being possible for the scanning itself to take place exclusively in the examination region of interest both as a purely circular scan without feed of the patient. The movement of the patient couch C8 relative to the gantry is effected by a suitable motorization. During this movement, the x-ray source C2 and/or C4 rotates in each instance about the patient. The detector C3 and/or C5 runs in parallel relative to the x-ray source C2 and/or C4, in order to detect projection measurement data which is then used to reconstruct sectional images. Alternatively to a sequential scan, whereby the patient is gradually moved through the examination field between the individual scans, it is also possible to use a spiral scan, whereby the patient is continuously moved along the system axis C9 through the examination field between x-ray tube C2 and/or C4 and detector C3 and/or C5 during the circumferential scanning with the x-ray radiation. The movement of the patient along the axis C9 and the simultaneous circulation of the x-ray source C2 and/or C4 produces a helical path relative to the patient during the measurement in the case of a spiral scan for the x-ray source C2 and/or C4. This path can also be achieved by the gantry being moved along the axis C9 when the patient is stationary. It is also possible to move the patient continuously and periodically to and fro between two points.

The CT system 10 is controlled by a control and computing unit C10 using computer program codes $Prg_1$ to $Prg_n$ which are present in a memory. Reference is made to these computer program codes $Prg_1$ to $Prg_n$ also being contained on an external storage medium and if necessary being loaded into the control and computing unit C10.

Acquisition control signals AS can be transmitted by the control and computing unit C10 by way of a control interface 24, in order to actuate the CT system C1 in accordance with specific measurement protocols. The acquisition control signals AS relate here for instance to: the x-ray tubes C2 and C4, with it being possible for details relating to their output and the time instances of their switch-on and switch-off being provided; as well as to the gantry, with it being possible to provide details relating to their rotational speed; and to the table feed.

Since the control and computing unit C10 has an input console, measurement parameters can be input by a user or operator of the CT device C1, which then control the data acquisition in the form of acquisition control signals AS. Information relating to currently used measurement parameters can be displayed on the monitor of the control and computing unit C10. In addition, further information which is relevant to the operator can be displayed.

The projection measurement data p and/or raw data acquired by the detector C3 and/or C5 is transferred to the control and computing unit C10 by way of a raw data interface C23. This raw data p is then, if necessary according to a suitable preprocessing, further processed in an image reconstruction component C21. In this exemplary embodiment, the image reconstruction component C21 is realized in the control and computing unit C10 in the form of software on a processor, e.g. in the form of one or more of the computer program codes $Prg_1$ to $Prg_n$. With respect to the image reconstruction, it is imperative, as already mentioned with respect to the control of the measurement process, that the computer program codes $Prg_1$ to $Prg_n$ also be contained on an external storage medium and if necessary that they can be loaded into the control and computing unit C10. It is also possible for the control of the measurement process and the image reconstruction to be implemented by different computing units.

The image data f, reconstructed by the image reconstruction component C21, is then stored in a memory C22 of the control and computing unit C10 and/or is conventionally output onto the monitor of the control and computing unit C10. The image data can also be fed into a network connected to the computed tomography system C1 by way of an interface (not shown in FIG. 1), for example a radiological information system (RIS), and can be stored in a mass storage device which is accessible there or output as images.

The control and computing unit C10 can also execute the function of an EKG, with a line C12 being used to dissipate the EKG potentials between patient and control and computing unit C10. In addition, the CT system C1 shown in FIG. 1 also has a contrast agent injector C11, by way of which additional contrast agent can be injected into the bloodstream of the patient, so that the vessels of the patient, in particular the ventricles of the beating heart, can be better displayed for example. Furthermore, there is herewith also the possibility of performing perfusion measurements, to which the proposed method is likewise suited.

Figure 2:
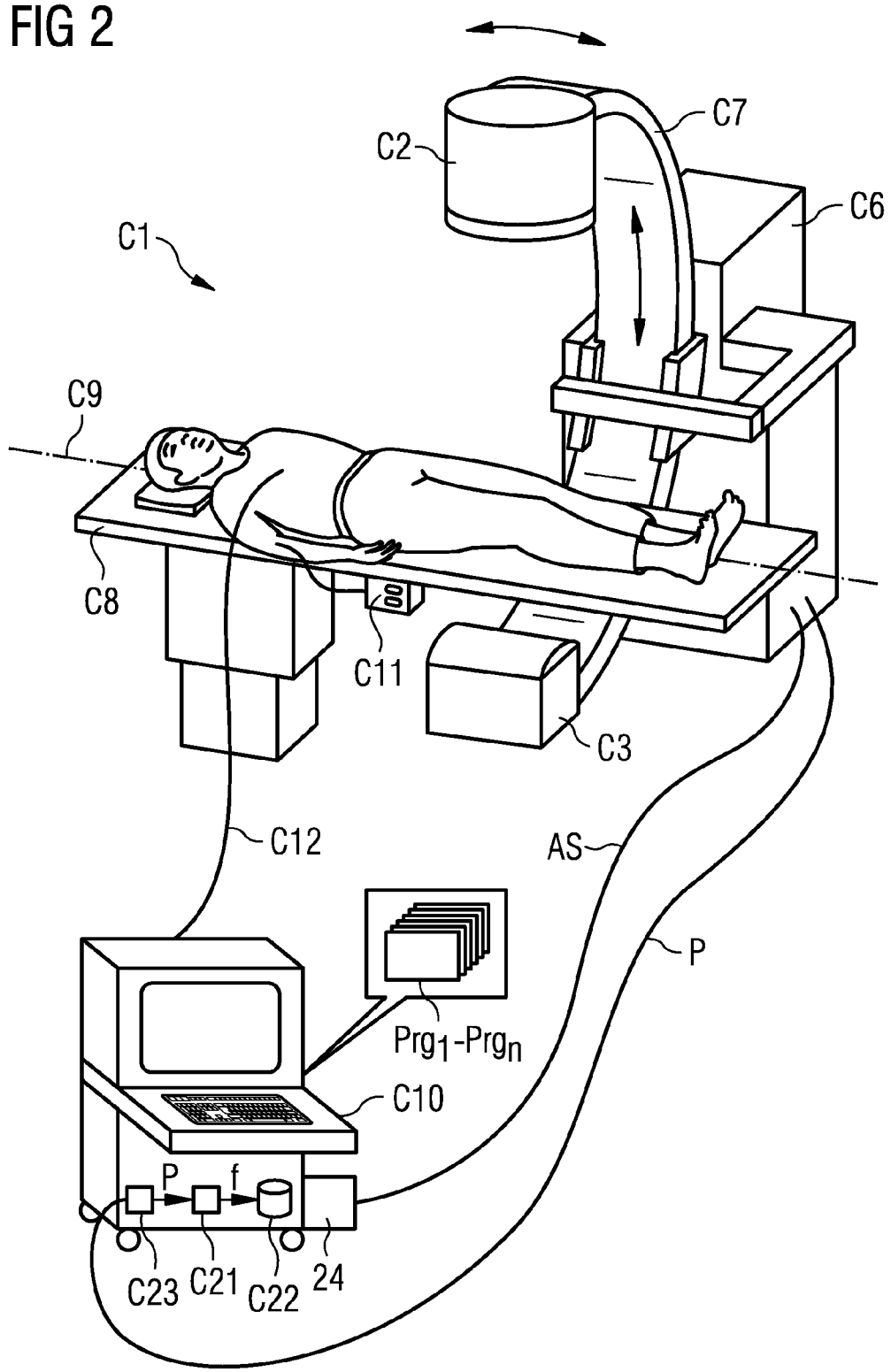
FIG. 2: shows a schematic representation of an exemplary embodiment of a computed tomography system with an image reconstruction component.

FIG. 2 shows a C-arm system, in which, contrary to the CT system in FIG. 1, the housing C6 supports the C-arm C7, to which on the one had the x-ray tube C2 and on the other hand the opposite detector C3 are fastened. The C-arm C7 is likewise pivoted about a system axis C9 for scanning, so that scanning can take place from a plurality of scanning angles and corresponding projection data p can be determined from a plurality of projection angles. The C-arm system C1 in FIG. 2, similarly to the CT system in FIG. 1, has a control and computing unit C10 of the type described in FIG. 1.

Example embodiments may be implemented in both systems shown in FIGS. 1 and 2. Furthermore, example embodiments may be used for other CT systems, e.g. for CT systems with a detector which forms a complete ring.

Because clinically relevant information is contained in the CT images reconstructed by the computing unit C10, it is particularly important for these images to be meaningful. For example, small tumors are also to be visible here, i.e. differ clearly from the surrounding tissue and be identifiable in respect of their size and position. Attempts are therefore made to perform a noise reduction in the CT images while simultaneously maintaining or even increasing the visibility of detailed information. With a reduced radiation dose and/or with the same dose, the same image quality and/or a higher image quality can herewith be achieved respectively.

The noise can be reduced in a CT image by smoothing image filters being used in the form of linear lowpass filters. Image sharpness may be reduced as because detailed information may be removed from the CT image. In order to estimate the image sharpness, it is possible to take account of the gradient of an edge in a CT image, which gradient corresponds to an ideal edge jump within the actual examination object. The steeper the edge within the CT image, the sharper the CT image. A smoothing taken place as a result of a noise reduction results in a blurring of the edge, so that the CT image's gradient and thus the image sharpness may reduce.

A method according to example embodiments is described below which reduces the noise in a CT image with a reduced and/or minimized reduction in sharpness. Simultaneously, the region around the edges is not excluded during the noise reduction. Instead, the noise reduction is also effective in these image regions. Furthermore, the noise reduction method does not change the CT-typical noise texture. CT images namely have a typical power noise spectrum, to which people evaluating the CT images, in particular radiologists, are accustomed. On account of this customary and/or training effect, it is undesirable to effect a basic change in the statistical properties of the image noise.

An iterative, non-linear image filter is used for noise reduction. A CT image $V_0$ is reconstructed from the measurement data, said CT image $V_0$ being referred to below as the image of the 0-th iteration. Known reconstruction algorithms may be used for image reconstruction, e.g. the FPB or an iterative reconstruction method. The image $V_0$ can be a two-dimensional sectional image or a three-dimensional volume image of the examination object. This also applies accordingly to the images $V_k$, which are calculated from the image $V_0$ as described below.

The iterative image filter is applied to the image of the 0-th iteration and then to the images $V_k$ calculated therefrom, in accordance with the following update equation:

$$V_{k+1} = V_k - \gamma_k \cdot V_k^E \quad \text{Equation (1)}$$

Where $V_{k+1}$ is the image of the (k+1)-th iteration, which is calculated from the image $V_k$ of the k-th iteration.

$\gamma_k$ is the filter strength in the iteration k. This is a number which can be changed from iteration to iteration. The filter strength $\gamma_k$ may however also remain constant, so that $\gamma_k = \gamma$. If $\gamma_k$ is changed as a function of the iteration, the $\gamma$-values can be changed in the course of the iteration for instance so that the regularization image $V_k^E$ contributes increasingly less to the image of the next iteration.

$V_k^E$ is a highpass-filtered version of the image of the k-th iteration, also referred to as a regularization image, whereby equation 2 (below) applies.

$$V_k^E(i) = \sum_{j=1}^{N} d_{ij} \cdot df_{ij} \cdot H(df_{ij} / \sigma^j(i)) \quad \text{Equation (2)}$$

Where i is the designation of an image element of the regularization image $V_k^E$, with the image elements of each image $V_k$ and $V_k^E$ being numbered from 1 to N. The totaling takes place across all pixels j. Instead of a total across all image elements, it is also possible to total all pixels j in the vicinity of pixel i. For example, a surface, e.g. the size of 3×3 image elements, or a volume, e.g. the size of 3×3×3 image elements, can be used about the image element i and the total can only be executed in this restricted part of the image.

The highpass characteristic of the image $V_k^E$ is generated by the domain filter $d_{ij}$, which can be given by the inverse distance of the image elements relative to one another for instance. Instead of the inverse distance, a different type of filter function with a highpass property can also be used.

$df_{ij}$ is the difference between the image element values of the image element i and image element j, in other words the contrast with respect to these two image elements i and j.

$\sigma^j(i)$ is the noise at image element 1 in the direction of image element j. In the case of CT images, it is possible to assume that no isotropic noise, but instead anisotropic and thus directional noise, exists at least in some image regions. This applies in particular to areas of the examination object with anisotropic attenuation. A direction with high noise corresponds to a direction with high statistical uncertainty, which comes about due to a strong attenuation of the x-ray beam.

In image element i, the local contrast-to-noise $df_{ij}/\sigma^j(i)$ relative to adjacent or if necessary also image elements which are further away, is determined. This contrast-to-noise $df_{ij}/\sigma^j(i)$ is weighted with the characteristic curve H. The characteristic curve H is herewith an integral part of the influence function.

The influence function $G=df_{ij}\cdot H(df_{ij}/\sigma^j(i))$ weights the highpass $d_{ij}$ as a function of the difference between image values of the respectively considered image element i and the image values of the direct or further adjacent image elements j. The influence function advantageously fulfills the properties $G(-x)=-G(x)$, i.e. it is asymmetrical and $G(\epsilon)>0$, i.e. for small positive values, G is positive.

A "normal" highpass filtering of the image takes place by using $d_{ij}$. The influence function brings about a deviation from "normal" highpass, namely as a function of the Contrast-to-Noise Ratio (CNR). The arguments of G are on the one hand the difference $df_{ij}$ of image values. On the other hand, $\sigma^j(i)$ is also used as an argument of G. It is advantageous to relate the difference of the image values to the local noise value in order, in this way, to execute the regularization independently of the local noise. To this end equation 3 (below) is defined.

$$G(t;\sigma^j) = \sigma^j(i)\cdot \tilde{G}\left(\frac{t}{\sigma^j(i)}\right) \qquad \text{Equation (3)}$$

An example of an influence function $\tilde{G}(t)$ is $$\tilde{G}(t) = \frac{t}{1+\left(\frac{|t|}{c_0}\right)^p} \qquad \text{Equation (4)}$$

Figure 3:
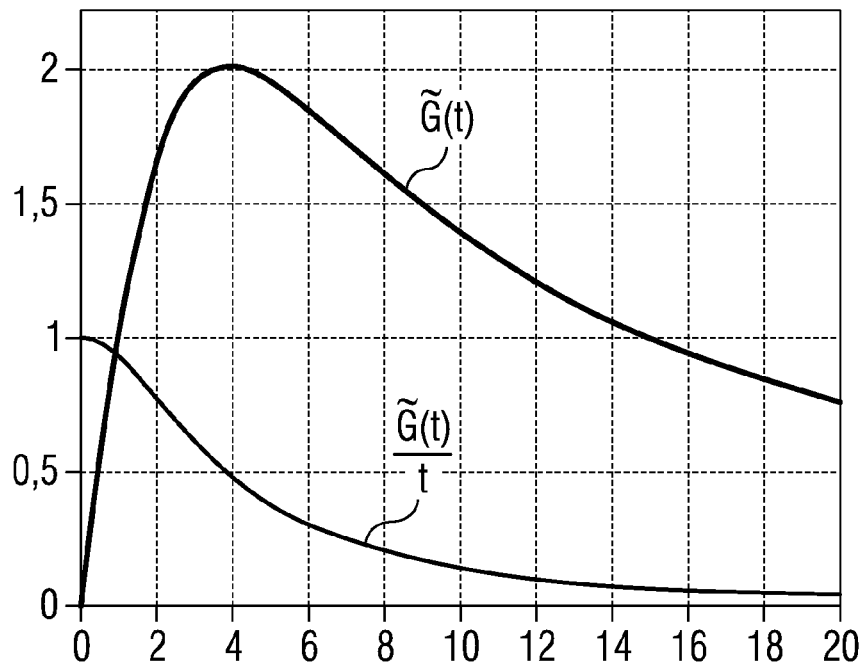
FIG. 3: shows an influence function according to at least one example embodiment.

FIG. 3 illustrates an influence function according to at least one example embodiment. As is shown in FIG. 3, $c_0=4$ and $p=2$ were selected and the influence function $\tilde{G}(t)$ is linear at the beginning, i.e. in the vicinity of value 0. In other words, image elements with a similar image value to the respectively considered image element influence the highpass filter linearly. This corresponds to the "normal" use of the highpass. With an increasing argument—this corresponds to a larger value deviation between the image value of an image element and the image value of the respectively considered image element at the site—the influence function deviates from the linearity. The influence function rises less than linearly in order finally to even drop away. Falling G-values mean that the respective image element is taken less into consideration during the highpass calculation. As a result of $\sigma^j(i)$ also influencing G, a highpass filter effect is achieved, which reduces with an increasing CNR.

The drop in the highpass effect is indicated in FIG. 3 by the curve $$\frac{\tilde{G}(t)}{t}.$$

The more this curve deviates from value 1, the more the influence function $\tilde{G}(t)$ deviates from the linearity. In equation (4), $c_0=4$ is the CNR at which the effect of the influence function on the value ½ has dropped, i.e. compared with a "normal" highpass, these image elements only still contribute the half.

The effect of the influence function from FIG. 3 is therefore that small and medium edges in the highpass-filtered image $V_k^E$ are included in accordance with the highpass filtering. By contrast, larger edges are only minimally considered during the highpass filtering so that they are barely visible in the highpass-filtered image $V_k^E$. The closer the influence function comes to value 0, the less significant the respective edges in the highpass-filtered image $V_k^E$.

It is even possible to select the influence function such that this changes its sign in the event of large arguments. An example of this is equation 5 below.

$$\tilde{G}(t) = \frac{t\cdot\left(1-\frac{t}{c_1}\right)}{1+\left(\frac{t}{c_0}\right)^p} \qquad \text{Equation (5)}$$

Figure 4:
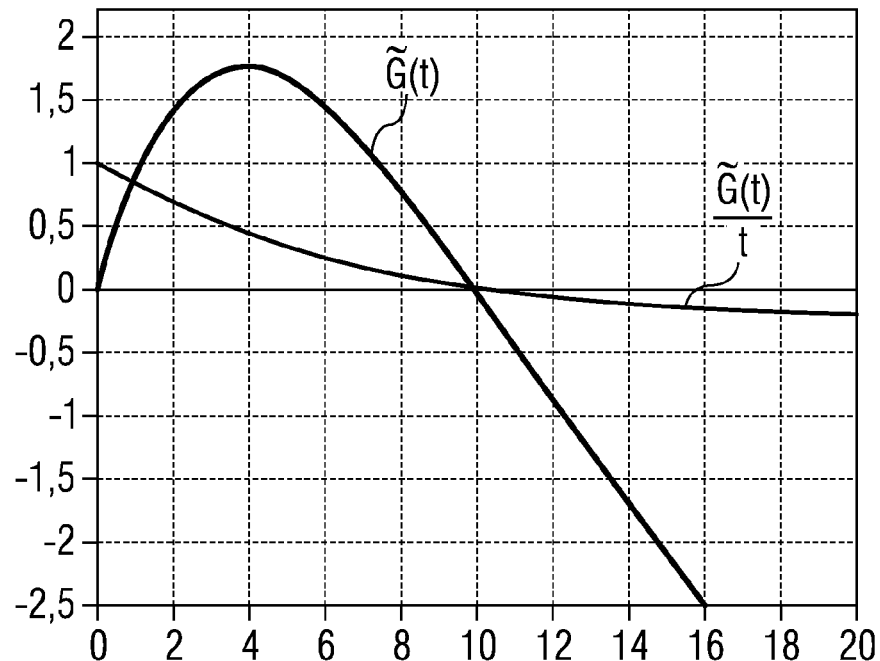
FIG. 4: shows an influence function according to at least one example embodiment.

This function is shown in FIG. 4 for $c_0=4$, $c_1=10$ and $p=1.5$. If the influence function changes the sign, this brings about a change in the sign of the filter coefficient of the highpass. A highpass filtering with a negative sign therefore takes place in respect of these large edges.

The influence function should be selected such that it rises linearly in order subsequently to rise less than linearly. This deviation from the linear rise may be so minimal that the rise in the influence function is also still positive for large arguments. The rise can however also change its sign (see FIG. 3), and the influence function can in this case also change its sign (see FIG. 4).

The described influence functions are only exemplary. The GGMRF priors (Generalized Gaussian Markov Random Field priors) represent another suitable class of influence functions for instance.

As a result of the image according to equation (1) filtered with the modified highpass being subtracted from image $V_k$, this functions as a lowpass filtering and thus a smoothing of the image $V_k$. A loud noise herewith brings about a stronger highpass effect and accordingly a stronger smoothing. The converse applies to large contrast values.

Equation (2) assumes that the anisotropic noise $\sigma^j(i)$ is known. The following describes how to obtain the anisotropic noise $\sigma^j(i)$. Two alternative procedures are presented here, which can however also complement one another in several components or can be exchanged.

For both procedures the noise $\sigma^j(i)$ is only determined in two dimensions, namely in the image plane of the image element i. If the image $V_k$ is a two-dimensional sectional image, this is therefore self-evident. If by contrast a three-dimensional volume image exists with $V_k$, which is composed of a plurality of two-dimensional sectional images, that plane which corresponds to the sectional image of the image element is considered in order to determine the noise $\sigma^j(i)$. For an image element j, which lies outside of this sectional image, this image element j is projected onto the image plane of the image element i in parallel with respect to the z-axis. The noise of the image element onto which the projection of the image element j strikes is then used as $\sigma^j$ with respect to this image element j.

The following equation applies for the first procedure:

$$(\sigma^j(i))^2 = \sigma(i)^2 \cdot \begin{pmatrix} \hat{\kappa}_{low} \\ \hat{\kappa}_{high} \end{pmatrix} \cdot \vec{e}^j(i) \quad \text{Equation (6)}$$

In other words, the noise variances $(\sigma^j(i))^2$ in the direction of the image element j are obtained from the aspect vector $$\begin{pmatrix} \hat{\kappa}_{low} \\ \hat{\kappa}_{high} \end{pmatrix},$$

with $\vec{e}^j(i)$ referring to the direction from image element i to image element j.

Figure 5:
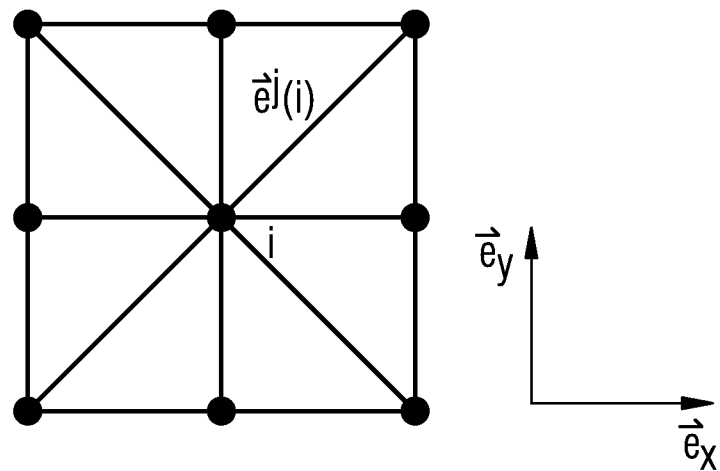
FIG. 5: shows adjacent image elements in a plane.

This direction $\vec{e}^j(i)$ is shown in FIG. 5, in which the 8 image elements adjacent to the centrally-positioned image element i are shown. 26 adjacent image elements would be present in three dimensions.

$\sigma(i)$ is herewith a variable which is a measure of the noise assumed as isotropic in image element i. Different methods can be used for this noise estimation, e.g. the following: variances along some lines running through the image element are calculated for each image element. The image values along a line are therefore regarded as a statistical ensemble and the variance of this ensemble is calculated. Several one-dimensional variances are therefore calculated in different spatial directions. The smallest of these variances is output as a result value $\sigma(i)$ for the respective image value i. The reason behind the use of the smallest value lies in a large variance value being obtained for lines which run through edges and/or existing structures. $\sigma(i)$ however indicates not the presence of structures in the surroundings of the respective image element, but makes available a measure of the noise. With the smallest variance value, it is possible to assume that this is typically formed by noise and not by structure.

It would alternatively also be possible to use a variable for $\sigma(i)$, said variable being independent of image element i.

The aspect vector $$\begin{pmatrix} \hat{\kappa}_{low} \\ \hat{\kappa}_{high} \end{pmatrix}$$

reproduces the main axes of a noise ellipse which is projected onto the Cartesian coordinate axes $\vec{e}_x$ and $\vec{e}_y$ (see FIG. 5).

The aspect vector is obtained as follows:

The image $V_k$ is projected forward into the data space so that entry into the sinogram space is achieved. The sinogram space represents a two-dimensional space per detector line, which is spanned on the one hand by the projection angle, i.e. the angular position of the x-ray source relative to the examination object, and on the other hand by the fan angle within the x-ray beam, i.e. by the position of the detector image element in the channel direction. The sinogram space therefore represents the domain of the measurement data, while the image space represents that of the image data.

The measured values of all projections are found in the sinogram, said projections running through the image element i on a sinusoidal line. By following this line, the maximum and minimum attenuation integrals are sought. The reason behind this is that a strong attenuation corresponds to a high noise value and a low attenuation corresponds to a low noise value. This herewith achieves equation 7 below.

$$k_{low} = \frac{1}{p^{low} + p^{high}} \cdot p^{low} \quad \text{Equation (7)}$$

and $$k_{high} = \frac{1}{p^{low} + p^{high}} \cdot p^{high}$$

Where $p^{low}$ is the smallest attenuation integral along the sinusoidal line, and $p^{high}$ is the largest attenuation integral along the sinusoidal line. Instead of individual values for $p^{low}$ and $p^{high}$, an averaging across a region of measured values adjacent to the sinusoidal line can be used. In this case the following equations apply.

$$k_{low} = \frac{1}{\sum p^{low} + p^{high}} \cdot \sum p^{low} \text{ and} \quad \text{Equation (8)}$$

$$k_{high} = \frac{1}{\sum p^{low} + p^{high}} \cdot \sum p^{high}$$

The vector $$\begin{pmatrix} k_{low} \\ \kappa_{high} \end{pmatrix}$$

specifies the length of the main axes of the noise ellipse. Here $k_{low}$ stands for a minimum value of the attenuation and $k_{high}$ for a maximum value of the attenuation.

After the length of the main axes has been determined, the directions associated herewith of the weakest attenuation $\vec{e}_{low}(i)$ and the strongest attenuation $\vec{e}_{high}(i)$ are taken from the sinogram. To this end, only the y-value of $p_{low}$ and $p_{high}$ must be read out from the sinogram, which corresponds to the respective fan angle within the x-ray beam and thus to the respective position of the detector pixel in the channel direction, in other words the projection angle. Similarly to the length of the main axes $$\begin{pmatrix} k_{low} \\ \kappa_{high} \end{pmatrix},$$

an averaging of measured values in the vicinity of the maximum and minimum of the attenuation can take place in order to determine $\vec{e}_{low}(i)$ and $\vec{e}_{high}(i)$. In this case the following equations apply:

$$\vec{e}_{low}(i) = \frac{1}{\sum p^{low}} \cdot \sum p^{low} \cdot \vec{e}^{low}(i) \quad \text{Equation (9)}$$

-continued and $$\vec{e}_{high}(i) = \frac{1}{\sum p^{high}} \cdot \sum p^{high} \cdot \vec{e}^{high}(i)$$

Where $\vec{e}^{low}(i)$ and $\vec{e}^{high}(i)$ refer to unit vectors in the directions of minimum and maximum attenuation.

The aspect vector $$\begin{pmatrix} \hat{\kappa}_{low} \\ \hat{\kappa}_{high} \end{pmatrix}$$

now results through a coordinate transformation of $$\begin{pmatrix} \vec{e}^{low}(i) \\ \vec{e}^{high}(i) \end{pmatrix}$$

by way of $$\begin{pmatrix} \hat{\kappa}_{low} \\ \hat{\kappa}_{high} \end{pmatrix} = \begin{pmatrix} (\kappa_{low} \cdot \vec{e}_{low}(i) + \kappa_{high} \cdot \vec{e}_{high}(i)) \cdot \vec{e}_x(i) \\ (\kappa_{low} \cdot \vec{e}_{low}(i) + \kappa_{high} \cdot \vec{e}_{high}(i)) \cdot \vec{e}_y(i) \end{pmatrix} \quad \text{Equation (10)}$$

Equation (10) can now be used in Equation (6) in order to achieve $\sigma^j(i)$.

It was assumed up to now that the noise in the image element i has an elliptical shape. This corresponds to the determination of solely two attenuation values and the directions associated therewith. Nevertheless, it is possible to take account of a larger number of directions, so that no elliptical shape generally exists.

With the second procedure for determining $\sigma^j(i)$, a standardized noise variable $\mu_i(\theta_j)$ is determined for the direction $\theta_j$ for each direction $\vec{e}_j$ with respect to an image element j with angle $\theta_j = \arccos(\vec{e}_j(i) \cdot \vec{e}_x)$:

$$\mu_i(\theta_j) = \frac{(\sigma^j(i))^2}{\sigma_0^2} = \frac{\exp(-p_0)}{\exp(-p_i(\theta_j))} \quad \text{Equation (11)}$$

The variable exp(−p) relates to an intensity and thus the actual measured variable, with p being the line integral and thus the attenuation value. It is not the intensities but instead the negative logarithms thereof, in other words the attenuation values p, which are usually entered into the sinogram. The values for $p_0$ and $p_i(\theta_j)$, which are to be used in Equation (11), are obtained from the sinogram as in the first procedure.

The noise $(\sigma^j(i))^2$ can therefore be specified from the ratio of the measured intensity $\exp(-p_i(\theta_j))$ to a standard intensity $\exp(-p_0)$, because in directions of strong attenuation, the projection data has lower statistical certainty and thus an increased noise.

$p_0$ is a standard attenuation, for instance the attenuation in a water phantom with a diameter of 30 cm, for which the noise $\sigma_0$ is achieved with the given core.

Figure 6:
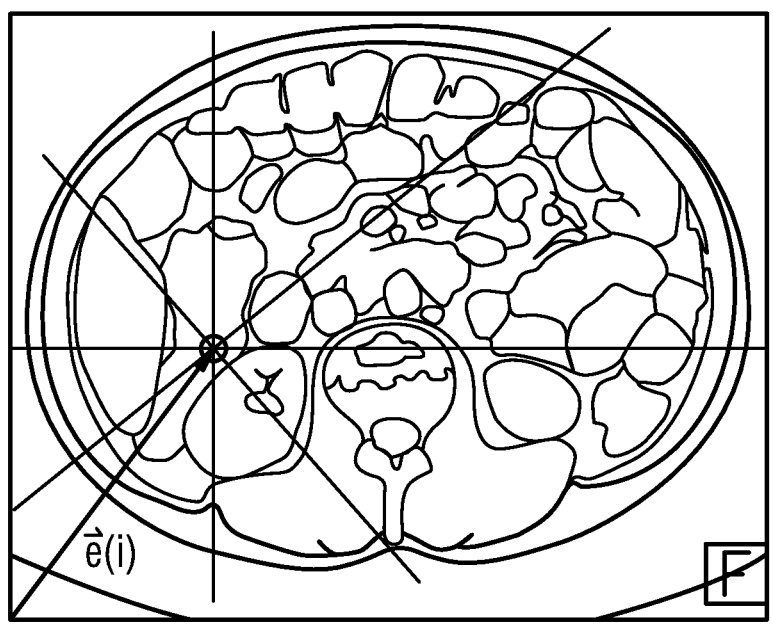
FIG. 6: shows a CT image.

$p_i(\theta_j)$ is the attenuation value on the sinus line of the image element i in the sinogram space, the y-value of which corresponds to the direction $\theta_j$. FIG. 6 shows a CT image, in which the projections which belong to the adjacent image elements in FIG. 5 are drawn. The attenuation values $p_i(\theta_j)$ corresponding to these projections are taken from the sinogram.

Instead of the first procedure, in which only two values are taken from the sinogram, namely the strongest and smallest attenuation, an attenuation value is now therefore used for each image element j.

The equations (2) therefore become $$V_k^E(i) = \sum_{j=1}^{N} d_{ij} \cdot df_{ij} \cdot H\left(\frac{df_{ij}}{\sigma_0 \cdot \mu_i(\theta_j)}\right) \quad \text{Equation (12)}$$

Here the term $$H\left(\frac{df_{ij}}{\sigma_0 \cdot \mu_i(\theta_j)}\right)$$

takes effect as described above, such that the smoothing preferably takes place in the direction in which the noise is great.

The qualitatively similar effect is also achieved with the use of the following regularization term:

$$V_k^E(i) = \sum_{j=1}^{N} d_{ij} \cdot df_{ij} \cdot \mu_i(\theta_j) \cdot H\left(\frac{df_{ij}}{\sigma_0 \cdot \mu_i(\theta_j)}\right) \quad \text{Equation (13)}$$

According to equation (13), the regularization strength above $\mu_i(\theta_j)$ is also directional. This means that the degree of the admixture of the regularization image $V_k^E$, which corresponds to the degree of the smoothing, is dependent on the size of the noise in a specific direction. The effect of the use of $\mu_i(\theta_j)$ on the one hand in the characteristic curve function H and on the other hand in the regularization strength is the same in terms of quality so that both of these mutually reinforce one another.

In both presented variants of the determination of $\sigma^j(i)$, the information relating to the direction of the noise was taken from the raw data.

After determining the anisotropic noise $\sigma^j(i)$, a new iteration image $V_k$ can be calculated by way of equations (1) and (2). The effect of the term $\gamma_k \cdot V_k^E$ in equation (1) is an anisotropic smoothing of the last iteration image $V_{k-1}$. This smoothing changes the noise behavior of the image $V_k$ compared to the image $V_{k-1}$. Strongly attenuating projections result in increased noise in their respective directions. As a result of the anisotropy of the noise being included in the lowpass filtering (see $V_k^E$), there is more significant smoothing in these directions.

This means that $\sigma^j(i)$ also changes from iteration to iteration. $\sigma^j(i)$ could be recalculated in each iteration in order to take account of this. Since this is however computationally intensive, it is proposed for simplicity reasons to use an iteration-dependent stretching factor $\delta_k$.

For the first procedure, Equation (6) in this case would become $$(\sigma^j(i))^2 = \sigma(i)^2 \cdot \left(\frac{\delta_k \cdot \hat{\kappa}_{low}}{\hat{\kappa}_{high}}\right) \cdot \vec{e}^j(i) \quad \text{Equation (14)}$$

Equation (11) in the second procedure would become $$\mu_i(\theta_j) = \frac{(\sigma^j(i) \cdot \delta_k)^2}{\sigma_0^2} \quad \text{Equation (15)}$$

$\delta_k$ can be changed from iteration to iteration in order to allow for the change in the noise behavior of the iteration images. Allowances are made here for the compositional directionality of the noise to reduce from iteration to iteration, i.e. with an increasing iteration, the noise equates to an isotropic behavior.

An embodiment of the invention describes a method for processing computed tomography image data, new image data is obtained by a noise-reducing processing of the image data, whereby a weighted highpass filtering of the image data takes place, with the weighting taking account, image element by image element, of an image noise on the respective image element in different directions such that increasing noise results in a stronger highpass effect. A noise-reducing smoothing of the image data takes place using the weighted highpass filtering.

The processing relates to computed tomography image data, in other words image data of an examination object which is reconstructed from measurement data which was acquired using a computed tomography system. A relative rotational movement between a radiation source of the computed tomography system and the examination object usually takes place during the measurement data acquisition process. Reconstruction methods may be used to calculate the image data from the measurement data, in particular a filtered backprojection method. The resulting image may be two or three-dimensional. This image is processed to reduce the image noise.

The noise-reducing processing includes at least two steps. On the one hand the weighted highpass filtering of the image data occurs. The weighting herewith brings about a deviation from a normal highpass filtering, e.g. using a Laplace filter. The deviation from the normal highpass filtering depends at least inter alia on the image noise. During the weighting, the noise on the respective image element is therefore taken into account per image element. This noise does not have to be an isotropic variable, which therefore has the same value irrespective of the considered direction. Therefore it is not only an individual noise value per image element which is considered but instead the noise in different directions. In other words, based on the respective image element, the different directions are considered and a noise value is used for each of the different directions. During the weighting of the highpass filtering, the noise is therefore used as the directional variable. The noise values may differ from direction to direction; it is however also possible that they are the same for many or all directions.

After calculating the weighted highpass filtering, a highpass-filtered image exists. This is used to implement a noise-reducing smoothing of the image data and thus obtain the new image data.

In an example embodiment, the weighting allows for, image element by image element, differences between an image element value of the respective image element and other image elements such that increasing differences result in a weaker highpass effect. Aside from the directional noises, differences between image element values of different image elements are taken into account during the weighting. Depending on how different the image element values of two image elements are, one of the image elements influences the calculation of the highpass-filtered value of the other image element to a greater or lesser extent. An increasing difference herewith results in a weaker highpass effect, at least in a specific value range of image element value differences.

According an example embodiment, the noise-reducing smoothing takes place using the weighted highpass filtering, in that the highpass-filtered image data is subtracted from the image data. With this differentiation, weighting factors can be used if necessary, i.e. the highpass-filtered image data can be multiplied by a factor which may, if necessary, vary from image element to image element, in order to be subtracted thus multiplied from the image data. The subtraction of highpass-filtered image data from the image data corresponds to a lowpass effect.

If the different directions are the directions relative to the adjacent image elements of the respective image element. Either neighbors in the image plane of the respective image element, in other words in two dimensions, or neighbors in three dimensions can herewith be considered. The adjacent image elements are preferably the direct neighbors of the image element; it is however also possible to include neighbors which are further apart. The neighbors considered are preferably those image elements which are used during the highpass filtering, i.e. if only the direct neighbors of an image element are taken into account during the highpass filtering, then during the weighting only the noise is used accordingly in these directions.

In an example embodiment, the image noise on the respective image element is determined in different directions, in that attenuation values associated with different directions are determined by the respective image element by consideration in the measurement data space. It is possible to reach this measurement data space by considering the original measurement data from which the image data to be smoothed was reconstructed. Alternatively, a forward projection of the image data into the measurement data space can also take place. During the computed tomography, attenuation integrals are measured by the examination object. Either these attenuation integrals or variables derived therefrom, e.g. the negative logarithm, can be displayed in the measurement data space. Accordingly, those attenuation values which relate to a specific image element, in other words the attenuation integrals running through this point, can be considered in the measurement data space.

In an example embodiment, a highest and a lowest attenuation value are determined in order herefrom to determine the image noise on the respective image element in the different directions. It is therefore determined, per image element, which is the highest and the lowest of the attenuation values. These maximum and minimum values can be determined by way of averaging across a region of high and low values. The attenuation values can then be determined from these two values in the different directions. The number of different directions is preferably greater than two.

In an example embodiment, an attenuation value is determined for each of the different directions, in order herefrom to determine the image noise on the respective image element in the respective direction. Contrary to the above procedure, a number of attenuation values which corresponds to the number of different directions is determined instead of two. Since the directions are known, the associated attenuation value can be easily determined in the measurement data space.

According an one example embodiment, the image noise, as a linear factor, influences the strength of the highpass effect. This means that louder noise in the linear degree brings about a stronger highpass effect. Aside from the linear influence, the image noise can also influence the highpass effect in other ways.

According to an example embodiment, the weighting takes place by using a function which rises linearly and with an increasing argument rises more weakly than linearly. If the function is considered in the direction of its increasing argument, it is firstly linear in the vicinity of the value 0 of the argument. Subsequently, i.e. with an increasing argument, the rise in the function drops compared with the linear curve. It is herewith possible for the function to firstly rise linearly and with an increasing argument to rise more weakly than linearly and with an even greater argument, to drop.

In this case, the rise in the function therefore changes its sign. It is also possible for the function to firstly rise linearly and with an increasing argument to rise more weakly than linearly and with an even greater argument to drop and with an even greater argument to change its sign. If the argument of the function contains the image noise, these different embodiments of the function enable this noise to influence the weighting of the highpass filtering in different ways. The argument of the function preferably contains the ratio between a difference between image element values of two image elements and the image noise. The highpass effect is in this way dependent on the anisotropic contrast-to-noise ratio on the respective image element.

If the acquisition of the new image data takes place by processing the image data without using the measurement data. This is contrary to an iterative reconstruction algorithm, whereby projection data is calculated according to an image calculation based on this image and is compared with the measurement data in order to calculate new image data between the calculated projection data and the measurement data using an existing deviation. By contrast, only the image data is currently needed in order to calculate image data improved therefrom without the measurement data being considered once again.

In an example embodiment, the new image data is output as result image data. According to the noise-reducing processing, image data is therefore already present which no longer forms the basis of a further calculation for reducing the image noise. Alternatively hereto, the new image data can subsequently also be subjected to the noise-reducing processing. The latter means that the same method steps, which were previously implemented based on the image data, for calculating the new image data are now implemented in order to further process the new image data. This is therefore an iterative image processing.

With an iterative image processing, it is possible to change the image noise on the respective image element in the different directions from one noise-reducing processing to another. This can take place by a renewed calculation of the image noise being implemented, as occurred with the first iteration. Alternatively, the noise values can be changed on the basis of specific assumptions by way of a change in the noise, which was caused by the noise-reducing processing.

According to at least one example embodiment, the noise-reducing processing brings about a contrast-dependent noise reduction in the image data. It is therefore not smoothed uniformly over the whole image, as a result of which sharpness would be lost. Instead, the noise is removed particularly at points of the image data which are low in contrast, while maintenance of the sharpness is observed in contrast-rich points.

An example embodiment of the control and computing unit is used to reconstruct the image data of an examination object from measurement data of a CT system. It includes a program memory for storing program codes, whereby a program code, if necessary inter alia, exists herein, which is suited to executing a method of the afore-described type or for effecting or controlling this execution. The inventive CT system includes such a control and computing unit. Furthermore, it can contain other components which are needed for instance to detect measurement data.

An example embodiment of the computer program has a program code which is suited to implementing the method of the afore-described type if the computer program is executed on a computer.

An example embodiment of the inventive computer program product includes a program code stored on a machine-readable data carrier, said program code being suited to implementing the method of the afore-described type if the computer program is executed on a computer.

While example embodiments have been particularly shown and described, it will be understood by one of ordinary skill in the art that variations in form and detail may be made therein without departing from the spirit and scope of the claims.

The invention claimed is:

1. A method for processing computed tomography image data, in which new image data is obtained by way of a noise-reducing processing of the image data, the method comprising:
    a weighted highpass filtering of the image data, with the weighting taking account, image element by image element, of a strength of an image noise on the respective image element in different directions;
    comparing a first image element to a next image element;
    increasing a highpass effect based on an increasing strength of noise of the weighted image elements; and
    controlling a noise-reducing smoothing of the image data using the weighted highpass filtering based on an amount of attenuation.

2. The method as claimed in claim 1, wherein the weighting takes account, image element by image element, of differences between an image element value of the respective image element and other image element values such that increasing differences result in a weaker highpass effect.

3. The method as claimed in claim 1, wherein
    the noise-reducing smoothing using the weighted highpass filtering is based on the highpass-filtered image data being subtracted from the image data.

4. The method as claimed in claim 1, wherein
    the different directions are directions relative to the adjacent image elements of a respective image element.

5. The method as claimed in claim 1, wherein the image noise on the respective image element is determined in the different directions, such that attenuation values associated with different directions are determined by the respective image element by consideration in the measurement data space.

6. The method as claimed in claim 5, wherein a largest and smallest attenuation value are determined from the attenuation values in order to determine the image noise on the respective image element in the different directions.

7. The method as claimed in claim 5, wherein an attenuation value is determined for each of the different directions, in order to determine the image noise on the respective image element in the respective direction.

8. The method as claimed in claim 1, wherein the image noise, as a linear factor, influences the strength of the highpass effect.

9. The method as claimed in claim 1, wherein the weighting takes place using a function which rises linearly and wherein an increasing argument rises more weakly than linearly.

10. The method as claimed in claim 9, wherein the function rises linearly, wherein an increasing argument rises more weakly than linearly and wherein an even greater argument drops.

11. The method as claimed in claim 9, wherein the function rises linearly, wherein an increasing argument rises more weakly than linearly and wherein an even greater argument drops and wherein an even greater argument changes its sign.

12. The method as claimed in claim 9, wherein the argument of the function contains the image noise.

13. The method as claimed in claim 9, wherein an argument of the function contains the ratio between a difference between image element values of two image elements and the image noise.

14. The method as claimed in claim 1, wherein the acquisition of the new image data takes place by processing the image data without using the original measurement data.

15. The method as claimed in claim 1, wherein the new image data is output as result image data.

16. The method as claimed in claim 1, wherein the new image data is subjected to the noise-reducing processing.

17. The method as claimed in claim 16, wherein the image noise on the respective image element is changed from noise-reducing processing to noise-reducing processing in the different directions.

18. The method as claimed in claim 1, wherein the noise-reducing processing effects a contrast-dependent noise reduction of the image data.

19. A control and computing unit for reconstructing image data of an examination object from measurement data of a CT system, the control and computing unit comprising:
  a program memory to store program codes, the program code existing in the program memory, to implements the method as claimed in claim 1.

20. A CT system comprising a control and computing unit as claimed in claim 19.

21. A non-transitory computer program product including program codes of a computer program, which are stored on a machine-readable data carrier, in order to implement the method as claimed in claim 1, when the computer program is executed on a computer.

22. The method of claim 1, wherein, during the weighted highpass filtering of the image data, the noise is used as a directional variable.

* * * * *